United States Patent
Birks et al.

(10) Patent No.: US 8,395,776 B2
(45) Date of Patent: Mar. 12, 2013

(54) OZONE MONITOR WITH GAS-PHASE OZONE SCRUBBER

(75) Inventors: John W. Birks, Boulder, CO (US); Peter C. Andersen, Superior, CO (US); Craig J. Williford, Golden, CO (US)

(73) Assignee: 2B Technologies, Inc., Boulder, CO (US)

( * ) Notice: Subject to any disclaimer, the term of this patent is extended or adjusted under 35 U.S.C. 154(b) by 299 days.

(21) Appl. No.: 12/512,763

(22) Filed: Jul. 30, 2009

(65) Prior Publication Data

US 2010/0027016 A1 Feb. 4, 2010

Related U.S. Application Data

(60) Provisional application No. 61/084,892, filed on Jul. 30, 2008.

(51) Int. Cl.
*G01N 21/00* (2006.01)
(52) U.S. Cl. ......... 356/437; 436/172; 436/166; 436/118
(58) Field of Classification Search .................. 356/437; 437/172, 166, 118
See application file for complete search history.

(56) References Cited

U.S. PATENT DOCUMENTS 4,018,562 A * 4/1977 Parks et al. .................... 436/114
5,571,724 A * 11/1996 Johnson ........................ 436/116
7,045,359 B2 * 5/2006 Birks et al. .................... 436/118

OTHER PUBLICATIONS

Meyer, C.P., Elsworth, C.M. & Galbally, I.E. (1991). "Water vapor interference in the measurement of ozone in ambient air by ultraviolet absorption." Review of Scientific Instruments, 62, 223-228.
Kleindienst, T., Hudgens, E., Smith, D., McElroy, F., & Bufalini, J. (Feb. 1993). "Comparison of Chemiluminescence and Ultraviolet: Ozone Monitor Responses in the Presence of Humidity and Photochemical Pollutants." J. Air Waste Manage. Assoc., 43, 213-222.
Leston, A. & Ollison, W. (1993). "Estimated Accuracy of Ozone Design Values: Are They Compromised by Method Interference?" Tropospheric Ozone: Nonattainment and Design Value Issues, Boston, MA; Proceedings of Air and Waste Management Association; TR-23, Air and Waste Management Association: Pittsburgh, PA; 451-456.

(Continued)

*Primary Examiner* — Tarifur Chowdhury
*Assistant Examiner* — Isiaka Akanbi
(74) *Attorney, Agent, or Firm* — Margaret Polson; Oppedahl Patent Law Firm LLC

(57) ABSTRACT

The present invention provides a means of greatly reducing or eliminating the interferences of UV-absorbing compounds, mercury, water vapor and particulates in the UV absorbance measurement of ozone by replacing the internal solid-phase ozone scrubber with a gas-phase scrubber. Reagent gases well suited as a gas-phase scrubber of ozone include nitric oxide and bromine atoms. Nitric oxide may be supplied by a gas cylinder or by photolysis of either $N_2O$ or $NO_2$, both in the absence of oxygen. Bromine atoms are conveniently generated by photolysis of $Br_2$ supplied by a permeation tube. Bromine atoms have the advantage of having a faster reaction with ozone than NO and of being catalytic in their reaction. Nitric oxide has the advantage of being generally less reactive with other components of air.

18 Claims, 5 Drawing Sheets

OTHER PUBLICATIONS

Hudgens, E.E., Kleindienst, T.E., McElroy, F.F., Ollison, W.M. (1994). "A Study of Interferences in Ozone UV and Chemiluminescent Monitors." International Symposium on Measurement of Toxics and Related Air Pollutants, Research Triangle Park, NC; Proceedings of the Air and Waste Management Association; VIP-39, Air and Waste Management Association: Pittsburgh, PA; 405-415.

Bognar, J.A. & Birks, J.W. (1996). "Miniaturized Ultraviolet Ozonesonde for Atmospheric Measurements." Analytical Chemistry, 68, 3059-3062.

Kleindienst, T.E., McIver, C.D., Ollison, W.M. (1997). "A Study of Interferences in Ambient Ozone Monitors." International Symposium on Measurement of Toxics and Related Air Pollutants, Research Triangle Park, NC; Proceedings of Air and Waste Management Association; VIP-74, Air and Waste Management Association: Pittsburgh, PA; 215-225.

Maddy, J.A. (Jun. 1998). "A Test That Identifies Ozone Monitors Prone to Anomalous Behavior While Sampling Hot and Humid Air." Paper presented at Air and Waste Management Association Annual Meeting, San Diego, CA.

Maddy, J.A. (1999) "Evaluating a Heated Metal Scrubber's Effectiveness in Preventing Ozone Monitor's Anomalous Behavior During Hot and Humid Ambient Sampling." Paper presented at Air and Waste Management Association Annual Meeting, St. Louis, MO.

United States Environmental Protection Agency, Office of Air Quality Planning and Standards. (Dec. 1999). Laboratory Study to Explore Potential Interferences to Air Quality Monitors. (25 pages).

Leston, A.R., Ollison, W.M., Spicer, C.W. & Satola, J. (2005). "Potential Interference Bias in Ozone Standard Compliance Monitoring." J. Air & Waste Manage. Assoc., 55, 1464-1472.

National Aeronautics and Space Administration, Jet Propulsion Laboratory. (Jul. 10, 2006). Chemical Kinetics and Photochemical Data for Use in Atmospheric Studies, Evaluation No. 15, NASA Panel on Data Evaluation.

Li, Y., Lee, S. & Wu, C. (2006) "UV-Absorption-Based Measurements of Ozone and Mercury: An Investigation on Their Mutual Interferences." Aerosol and Air Quality Research, 6(4), 418-429.

Wilson, K.L. & Birks, J.W. (2006). "Mechanism and Elimination of a Water Vapor Interference in the Measurement of Ozone by UV Absorbance." Environmental Science and Technology, 40(20), 6361-6367.

U.S. Appl. No. 12/595,930, filed Oct. 14, 2009, First Named Inventor: Peter C. Andersen.

U.S. Appl. No. 12/480,544, filed Jun. 8, 2009, First Named Inventor: John W. Birks.

* cited by examiner

OZONE MONITOR WITH GAS-PHASE OZONE SCRUBBER

CROSS REFERENCE TO RELATED APPLICATIONS

This application is a non-provisional application claiming the benefits of provisional application No. 61/084,892 filed Jul. 30, 2008.

BACKGROUND

Ozone is a toxic gas produced in photochemical air pollution as a result of a complex sequence of reactions involving oxides of nitrogen, hydrocarbons and sunlight. The Clean Air Act in the U.S. and similar laws in other countries set limits on ozone concentrations in ambient air. Enforcement of compliance with the U.S. National Air Quality Standard requires continuous monitoring of ozone concentrations. Compliance monitoring is done almost exclusively by the method of UV absorbance of the Hg emission line at 254 nm. Low pressure mercury lamps provide an intense, stable and inexpensive source of radiation very near the maximum in the ozone absorption spectrum.

It is well known that ozone monitors based on UV absorbance suffer from interferences from other species that absorb at 254 nm. Volatile organic compounds (VOCs) that interfere are generally aromatic compounds. Some VOCs have a larger response at 254 nm than ozone itself. For example, Kleindienst et al. (1993) reported that the response of 2-methyl-4-nitrophenol is about 40% higher than ozone. Mercury provides a particularly strong interference because the electronic energy levels of Hg atoms are resonant with the Hg emission line of the low pressure Hg lamp used in ozone monitors. The relative response to Hg as compared to ozone depends on the temperature and pressure of the lamp and on the efficiency with which the instrument's internal ozone scrubber removes mercury, but is usually in the range 100-1000. The U.S. EPA (1999) reported that at a baseline ozone concentration of approximately 75 parts per billion (ppb), the presence of 0.04 ppb Hg (300 ng/m$^3$ at room temperature) caused an increase in measured ozone concentration of 12.8% at low humidity (RH=20-30%) and 6.4% at high humidity (RH=70-80%) using a UV photometric ozone monitor. For dry air, Li et al. (2006) found that 1 ppb of mercury gave a response equal to approximately 875 ppb of ozone in the same model of Thermo Electron Corporation photometric ozone monitor used in the EPA study. This mercury interference can be quite large inside buildings where mercury vapor may be present as a result of past mercury spills (broken thermometers, fluorescent light fixtures, electrical switches, etc.), near mining operations and near various industrial facilities.

Another way in which mercury interferes in the measurement of ozone using ozone photometers is by adsorption and desorption from the instrument's internal ozone scrubber. These scrubbers are typically composed of manganese dioxide, charcoal, hopcalite or heated silver wool. Mercury atoms will adsorb to and accumulate on the surfaces of the scrubber material. If the temperature of the scrubber increases, or if the humidity changes, the mercury atoms may be released from the scrubber and enter the gas stream. While removal of mercury vapor from the sample stream by the scrubber will cause a positive interference, release of mercury from the scrubber will cause a negative interference. Since mercury is present at some level in all outdoor and indoor air, this interference may be responsible for much of the baseline drift that occurs in photometric ozone monitors.

A water vapor interference in the measurement of ozone by UV absorption has been described by several investigators (Meyer et al., 1991; Kleindienst et al., 1993; Leston and Ollison, 1993; Leston et al., 2005; Hudgens et al., 1994; Kleindienst et al., 1997; Maddy, 1998; Maddy, 1999; U.S. Environmental Protection Agency, 1998; Wilson and Birks, 2006). Recent studies have shown that this interference, which may amount to up to several tens of ppb of ozone, is caused by physical effects by water vapor on the transmission of light through the detection cell (Wilson and Birks, 2006). Depending on the humidity history, the solid-phase ozone scrubber can either add or remove water vapor from the flow stream during the measurement of reference lamp intensity, thereby affecting the calculated ozone concentration. Consistent with this hypothesis, it was found that reducing the mass of the ozone scrubber material greatly reduced the degree of interference (Wilson and Birks, 2006).

This invention provides a means of reducing interferences from Hg, UV-absorbing organic compounds, particles and water vapor to negligible levels by replacing the solid-phase ozone scrubber used in UV-absorbance-based ozone monitors with a gas-phase ozone scrubber. In particular, nitric oxide (NO) can be added to the sample stream to serve as the gas-phase scrubber.

The foregoing example of the related art and limitations related therewith are intended to be illustrative and not exclusive. Other limitations of the related art will become apparent to those of skill in the art upon a reading of the specification and a study of the drawings.

SUMMARY

One aspect of this invention is the measurement of ozone concentrations by UV absorbance in which the solid-phase ozone scrubber is replaced by a gas-phase scrubber.

Another aspect of this invention is the use of nitric oxide gas in combination with a reaction volume as a gas-phase ozone scrubber for photometric ozone monitors.

Another aspect of this invention is the use of bromine atoms produced in the photolysis of diatomic bromine in combination with a reaction volume as a gas-phase ozone scrubber for photometric ozone monitors.

The following embodiments and aspects thereof are described and illustrated in conjunction with systems, tool and methods which are meant to be exemplary and illustrative, not limiting in scope. In various embodiments, one or more of the above described problems have been reduced or eliminated, while other embodiments are directed to other improvements.

Disclosed herein is a method for measuring ozone by UV absorbance in which the solid phase scrubber is replaced by a gas-phase scrubber in order to reduce interferences of Hg, UV-absorbing compounds, particulate matter and water vapor to negligible levels.

In addition to the exemplary aspects and embodiments described above, further aspects and embodiments will become apparent by reference to the accompanying drawings forming a part of this specification wherein like reference characters designate corresponding parts in the several views.

Before explaining the disclosed embodiment of the present invention in detail, it is to be understood that the invention is not limited in its application to the details of the particular arrangement shown, since the invention is capable of other embodiments. Exemplary embodiments are illustrated in referenced figures of the drawings. It is intended that the embodiments and figures disclosed herein are to be considered illustrative rather than limiting. Also, the terminology used herein is for the purpose of description and not of limitation.

DETAILED DESCRIPTION

Figure 1:
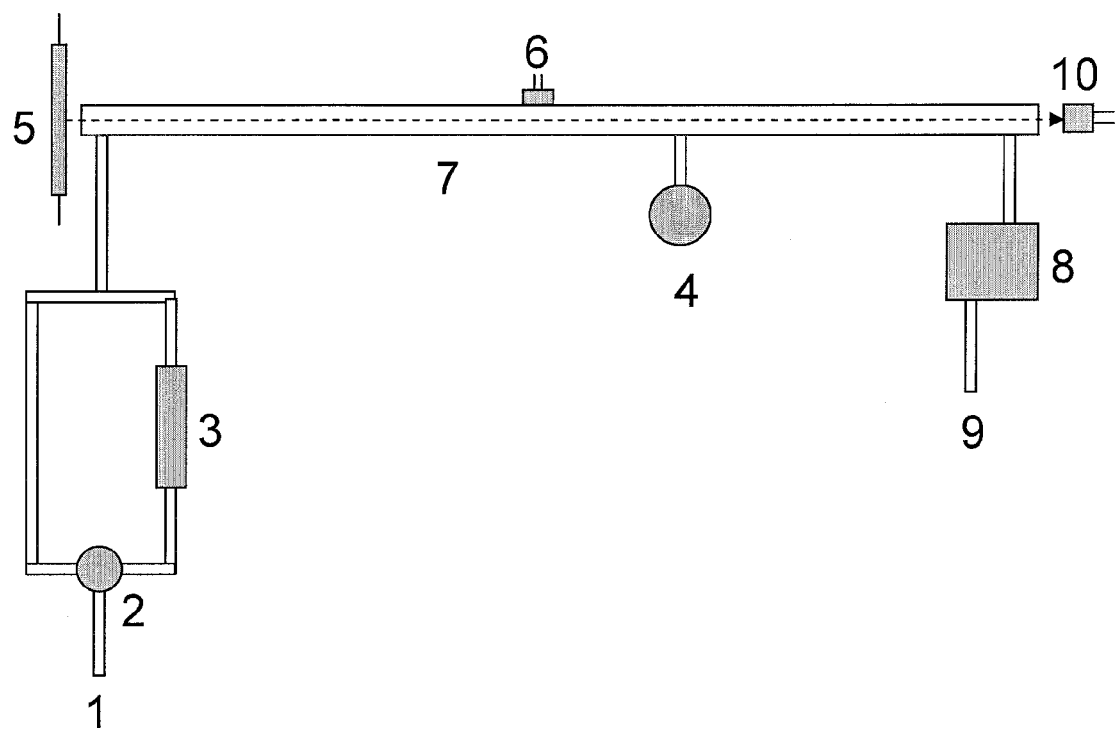
FIG. 1 is a schematic diagram of a typical single-beam UV absorbance instrument for measurement of ozone concentrations in air.

A schematic diagram of a typical single-beam UV-absorbance photometer for measuring ozone is provided as FIG. 1. Sample air flows through the instrument, entering through the inlet 1 and exiting the outlet 9. Ozone is measured based on the attenuation of light passing through a flow-through absorption cell 7 fitted with quartz windows or other UV-transparent windows. A low-pressure mercury lamp 5 is located on one side of the absorption cell 7, and a photomultiplier, photodiode or other light sensing detector 10 is located on the opposite side of the absorption cell 7. Typically, an interference filter (not shown) is placed in front of the photodetector to isolate the 254 nm Hg line. Some photodiodes are made with a built-in interference filter centered at 254 nm specifically for detection using a mercury lamp. In this diagram, an air pump 8 continuously draws sample air into the instrument. In one miniature ozone monitor, a fan has been used in place of the air pump (Bognar and Birks, 1996). A solenoid valve 2 switches so as to alternately send sample air either directly through the absorption cell 7 or through an ozone scrubber 3 and then through the absorption cell. The intensity of light at the photodetector 10, $I_o$, is measured for air that has passed through the ozone scrubber 3, and the attenuated light intensity, I, is measured for air that has bypassed the scrubber. Ozone concentration is calculated from the measurements of $I_o$ and I according to the Beer-Lambert Law:

$$C_{O_3} = \frac{1}{\sigma l}\ln\left(\frac{I_o}{I}\right) \tag{1}$$

where l is the path length (typically 5-50 cm) and $\sigma$ is the absorption cross section for ozone at 254 nm ($1.15\times10^{-17}$ cm$^2$ molecule$^{-1}$ or 308 atm$^{-1}$ cm$^{-1}$), which is known with an accuracy of approximately 1%.

The pressure and temperature within the absorption cell are measured using a pressure sensor 4 and a temperature sensor 6 so that the ozone concentration can be expressed as a mixing ratio in parts-per-billion by volume (ppb). In principle, the measurement of ozone by UV absorption requires no external calibration; it is an absolute method. However, non-linearity of the photodiode response and electronics can result in a small measurement error. Therefore, ozone monitors are typically calibrated relative to an ozone standard such as one of the reference photometers maintained by the U.S. National Institute of Science and Technology (NIST).

Dual beam instruments for ozone measurements also are common. In a dual beam instrument, ozone-scrubbed air passes through one detection cell while sample air passes through the second detection cell. The flow path is periodically changed using switchable valves so that I and $I_o$ are alternately measured in each cell. Compared to a single-beam instrument, dual beam instruments provide faster measurements than single-beam instruments, and precision may be improved due to cancellation of lamp fluctuations. Typically, dual beam instruments have better precision for the same data averaging time and better baseline stability. Various plumbing variations for dual beam ozone monitors are known; for example, rather than using parallel flow paths through the two detection cells, a single sample flow may pass through one detection cell followed by an ozone scrubber followed by the second detection cell and valves used to periodically reverse the direction of flow.

Both single beam and dual beam ozone monitors suffer from interferences from mercury vapor, various organic compounds, particles such as smoke and dust, and water vapor. If a UV-absorbing, gas-phase or particulate species is present at equal concentrations during I and $I_o$ measurements, then $I=I_o$ and according to equation 1 the measured contribution to absorbance will be zero and that species will not interfere. However, nearly all chemical species are at least partially removed by the internal ozone scrubber 3 of FIG. 1, thus modulating the detected light intensity and causing any UV-absorbing species to contribute to the measured absorbance. The purpose of the present invention is to greatly reduce, often to insignificant levels, the interferences of gas-phase and particulate-phase interferences in ozone measurements by replacing the solid-phase ozone scrubber with a gas-phase scrubber.

Figure 2:
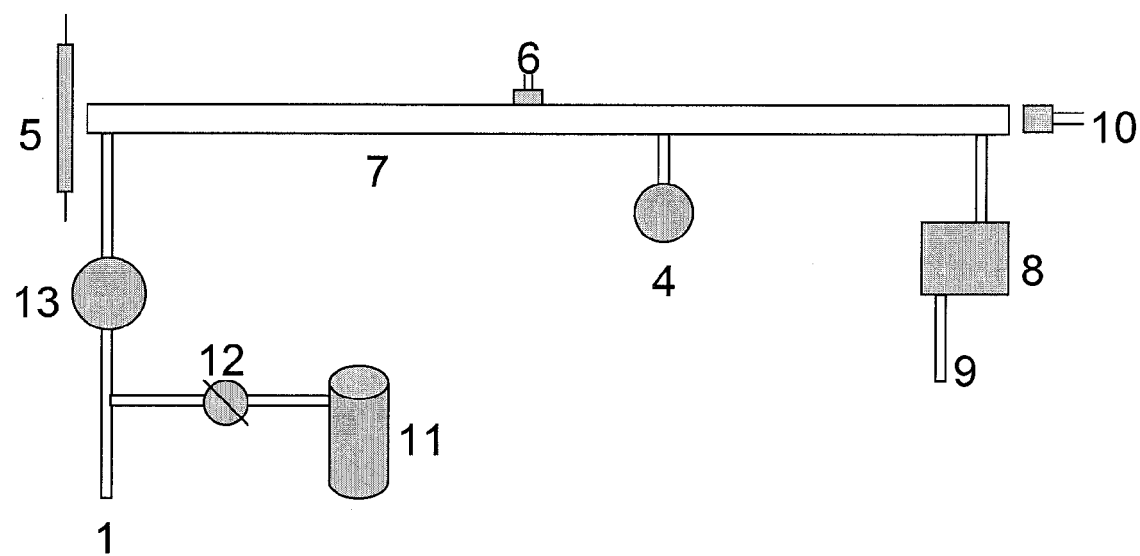
FIG. 2 is a schematic diagram of a single-beam ozone monitor with the solid-phase scrubber replaced by a gas-phase scrubber.

In the present invention, the solid-phase ozone scrubber of FIG. 1 is replaced by the gas-phase scrubbing process of FIG. 2 where a reagent gas X is added from source 11 via valve 12. Valve 12 allows gas X to enter the gas stream and mix with ozone in the sample gas. X reacts with ozone to destroy it via the reaction:

$$X+O_3 \rightarrow XO+O_2 \tag{2}$$

Examples of X include nitric oxide (NO) and the halogen atoms F, Cl, Br and I. Flow through the reaction volume 13 allows sufficient time for the reaction to be substantially complete. A nearly complete reaction is desirable, but not necessary if the flow rates of gases are held constant. The extent of reaction can be calculated from the reaction volume, V, total volumetric flow rate, F, reagent gas concentration, [X], and second order reaction rate constant, k. For example, if NO is the reagent gas X and the reaction is made pseudo-first order with [NO]>>[$O_3$], the fraction of ozone unreacted after passing through the reaction volume is given by $$\frac{[O_3]}{[O_3]_o} = e^{-k[NO]V/F} \tag{3}$$

where $[O]_o$ is the ozone concentration prior to reaction. For example, for a NO mixing ratio of 4 parts-per-million, a reaction volume of 50 cm³, flow rate of 1 L/min, rate constant for the NO+O₃ reaction of $1.8 \times 10^{-14}$ cm³ molec⁻¹ s⁻¹, ambient pressure and temperature of 25° C., $[O_3]_o$ is calculated to be 0.005. In other words, the reaction is 99.5% complete. For this example, the reaction time, V/F, is 3 seconds. Thus, reaction conditions can be adjusted to achieve nearly or substantially complete destruction of ozone when NO is used as the reagent gas.

Ozone is measured by alternating opening and closing valve 12. When the valve is open (NO allowed to flow), ozone is substantially destroyed and the analytical signal $I_o$ is measured. When the valve is closed, no ozone is destroyed and the analytical signal I is measured. The concentration of ozone may then be calculated using equation 1 and applying appropriate calibration factors.

Because of the dilution effect of the added reagent gas, the contributions to absorbance by interfering compounds will be different during scrubbed ($I_o$) and unscrubbed (I) measurements. Thus, the contribution to absorbance by an interference will be reduced by the factor R as follows:

$$R = \frac{F_{Sample} + F_{Reagent}}{F_{Reagent}} \quad (4)$$

Figure 3:
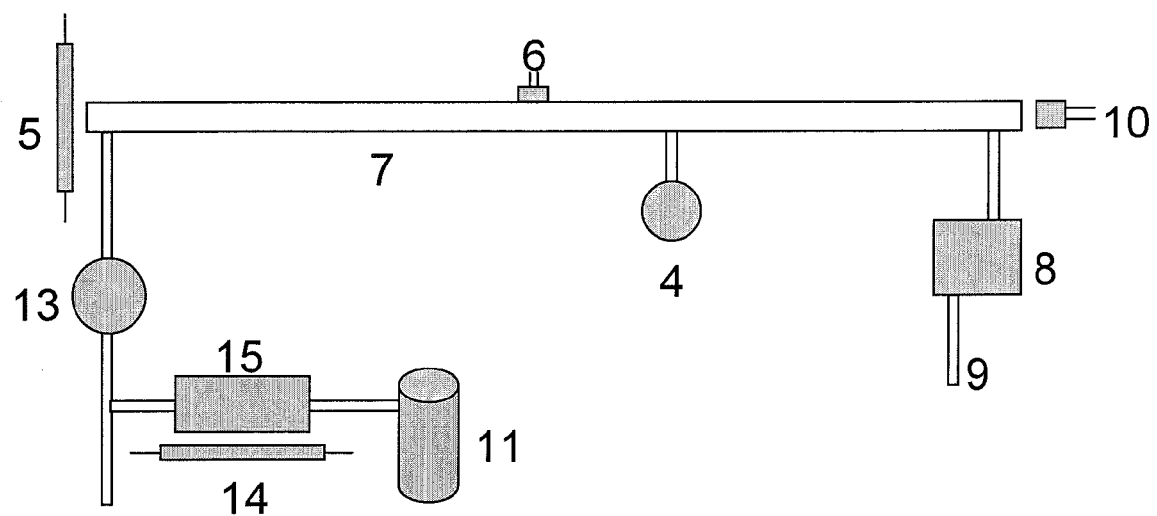
FIG. 3 is a schematic diagram of a single-beam ozone monitor with the solid-phase ozone scrubber replaced by a gas-phase scrubber where the reactant gas is generated by photolysis of a precursor gas supplied by a permeation tube.

In other words, if the reagent flow makes up 1% of the total flow, the absorbance from interferences is reduced by a factor of 100. Interferences can be completely cancelled if the reagent flow is matched by a flow of ozone-scrubber air or other inert gas during the period that the reagent flow is turned off. In that case valve 12 may be a 3-way valve that switches between reagent gas from source 11 and ozone-depleted gas from another source. Of course, the dilution factor must be accounted for in computing the ozone concentration. This is conveniently done if the reagent gas is generated photochemically since the photolysis lamp may be modulated to add and remove the reagent gas as shown in FIG. 3. Here a reagent gas supplied by the source 11 passes through the photochemical reactor 15 where it is photolyzed by lamp 14 to produce a species that reacts with ozone. In order to switch between measuring ozone-scrubbed (intensity $I_o$) and unscrubbed (intensity I) air (or other sample gas), the lamp is simply turned on and off. Thus, the ozone concentration is modulated, but interferences that do not react with the photolysis products are not modulated and their contribution is completely eliminated. As an example, NO could be produced by photolyzing N₂O in photolysis chamber 15 using a low pressure mercury lamp:

$$N_2O + h\nu \rightarrow N_2 + O(^1D_2) \quad (5)$$

$$O(^1D_2) + N_2O \rightarrow 2NO \quad (6)$$

Net: $2N_2O + h\nu \rightarrow N_2 + 2NO$ (7)

Alternatively, NO may be produced from NO₂ by photolysis using a black lamp with emissions centered at 366 nm or by use of a near UV light emitting diode:

$$NO_2 + h\nu \rightarrow NO + O \quad (8)$$

$$O + NO_2 \rightarrow NO + O_2 \quad (9)$$

Net: $2N_2O \rightarrow 2NO + O_2$ (10)

This reaction must be carried out in the absence of oxygen; otherwise ozone will be produced from combination of the O atom produced in reaction 8 with oxygen. The use of NO₂ as a source of NO has the advantage that it can be supplied by a permeation tube. Nitrous oxide (N₂O) has the advantage of being much less toxic. Nitrous oxide is available in small cartridges used for making whipped cream and is a consumer product.

Other reagent gases may be used to effectively scrub ozone. The rates of reactions of halogen atoms with ozone, for example, are much larger than that of NO so that the reaction times required are much shorter. At 25° C. the reaction rate coefficients are $1.0 \times 10^{-11}$, $1.2 \times 10^{-11}$, $1.2 \times 10^{-12}$ and $1.2 \times 10^{-12}$ cm³ molec⁻¹ s⁻¹ for the reactions of F, Cl, Br and I atoms with ozone, respectively (NASA, 2006). In addition, halogens are catalytic in their reactions with ozone via the sequence of reactions, $$(X + O_3 \rightarrow XO + O_2) \times 2 \quad (11)$$

$$XO + XO \rightarrow 2X + O_2 \quad (12)$$

Net: $2O_3 \rightarrow 3O_2$ (13)

thus reducing the concentration of halogen atom required to efficiently destroy ozone within a given reaction time. Halogen atoms are easily produced by photolysis of the corresponding diatomic halogen molecules, F₂, Cl₂, Br₂ and I₂ as follows:

$$X_2 + h\nu \rightarrow 2X \quad (14)$$

Although any of the diatomic halogens could be used as a source of halogen atoms, Br₂ is considered the most suitable for use as a gas-phase scrubber. Fluorine is the most corrosive of the halogens and is difficult and even dangerous to handle. It is a gas at room temperature and atmospheric pressure and thus cannot be supplied by a permeation tube. Iodine is a solid at room temperature and atmospheric pressure. Sufficient vapor pressure could be obtained by heating, but because of its low vapor pressure it will condense onto cooler surfaces throughout the apparatus unless the entire flow path is heated. Permeation tubes may be produced that contain either chlorine or bromine in liquid form. The ClO product formed in the reaction of Cl atoms with O₃ absorbs strongly at 254 nm, the same wavelength used for ozone detection. This absorption by the ClO product is calculated to reduce the sensitivity to ozone by up to 37% and introduce uncertainty since some of the ClO would be lost to its disproportionation reaction and possibly other reactions. Bromine has a much larger absorption cross section than chlorine in the near UV where inexpensive light sources such as black lamps and UV LEDs are readily available, and BrO does not absorb significantly at 254 nm. Also, the catalytic reaction sequence described by reactions 11-13 is much faster for bromine atoms than for chlorine atoms. The rate determining step, reaction 12, has a rate coefficient of $2.7 \times 10^{-12}$ cm$^3$ molec$^{-1}$ s$^{-1}$ for the BrO+BrO reaction and $8.5 \times 10^{-15}$ cm$^3$ molec$^{-1}$ s$^{-1}$ for the ClO+ClO reaction (NASA, 2006). Thus, the BrO+BrO reaction is more than 300 times faster. Both reactions form products other than $2X+O_2$ that don't propagate the chain. In the case of bromine, the branching ratio to the products $2Br+O_2$ is 85% compared to 49% for the products $2 Cl+O_2$ in the case of chlorine (NASA, 2006). Clearly, bromine is a better catalyst than chlorine for ozone destruction, a fact well known with respect to relative effects of chlorine and bromine on ozone depletion in the stratosphere.

Figure 4:
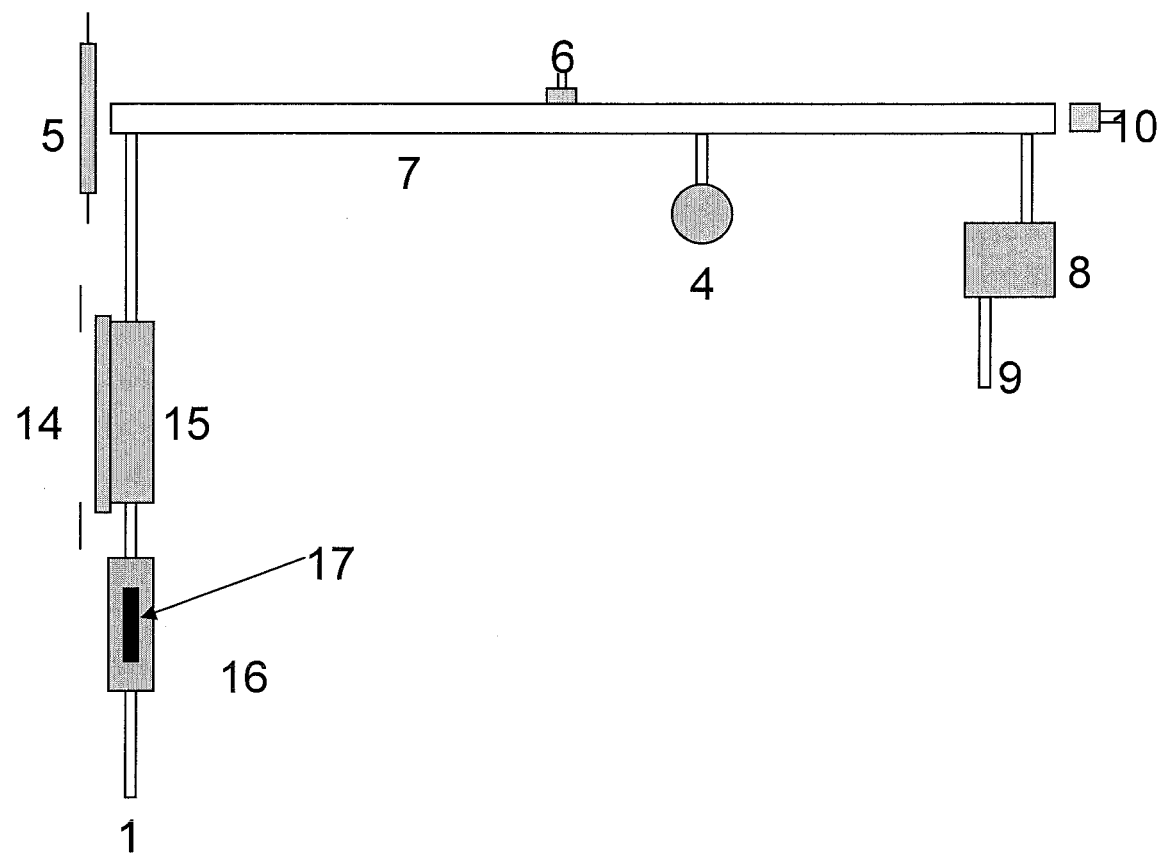
FIG. 4 is a schematic diagram of a single-beam ozone monitor with the solid-phase ozone scrubber replaced by a gas-phase scrubber where the reactant gas is generated by photolysis of a precursor gas supplied in-line by a permeation tube.

FIG. 4 is a schematic diagram of a ozone monitor that makes use of a gas phase scrubber in which a reagent gas is released by a permeation tube and photolyzed to produce a species that rapidly reactions with ozone. The advantage of this approach over that of FIG. 3 is that the reagent is added with no significant dilution and thus no correction for dilution of the sample is required. The gas sample containing ozone to be measured passes through chamber 16 containing a permeation tube 17. The gas sample containing reagent gas supplied by the permeation tube next passes through a combined photolysis and reaction chamber 15 where light from the radiation source causes the reagent to photolyze to produce one or more species that react with ozone. Ozone is measured by modulating the lamp. When the lamp is off, no ozone is destroyed and the analytical signal $I_o$ is measured. When the lamp is on, nearly of the ozone is destroyed and the analytical signal I is measured. The concentration of ozone may then be calculated using equation 1 and applying appropriate calibration factors.

Other reagents for ozone destruction may be derived from photolysis of relatively stable compounds. Some examples include $H_2O_2$ and $HNO_2$ (HONO, nitrous acid). Hydrogen peroxide, which may be supplied by a permeation tube, photolyzes to produce two hydroxyl radicals, which undergo a relatively fast reaction with ozone:

$$H_2O_2 + h\nu \rightarrow 2\ OH \qquad (8)$$

$$OH + O_3 \rightarrow HO_2 + O_2 \qquad (9)$$

Nitrous acid photolyzes to produce OH and NO, both of which react with ozone, as discussed above:

$$HONO + h\nu \rightarrow OH + NO \qquad (10)$$

Alkenes and aromatic compounds also are known for their reactions with ozone, although the gas-phase reaction rates are relatively slow. One skilled in the art would be aware of many other species that react with ozone that may potentially serve as the reagent for a gas-phase scrubber.

Of the reagents discussed above, the preferred reagents are NO and Br atoms. An advantage of NO is that it has no known reactions with any potentially interfering compounds in ambient air. Although the vapor pressure of NO is too high for a permeation tube, it can be produced by photolysis of $N_2O$ or $NO_2$, as discussed earlier. Bromine may be supplied in-line from a permeation tube and photolyzed to produce Br atoms.

EXAMPLE

Figure 5:
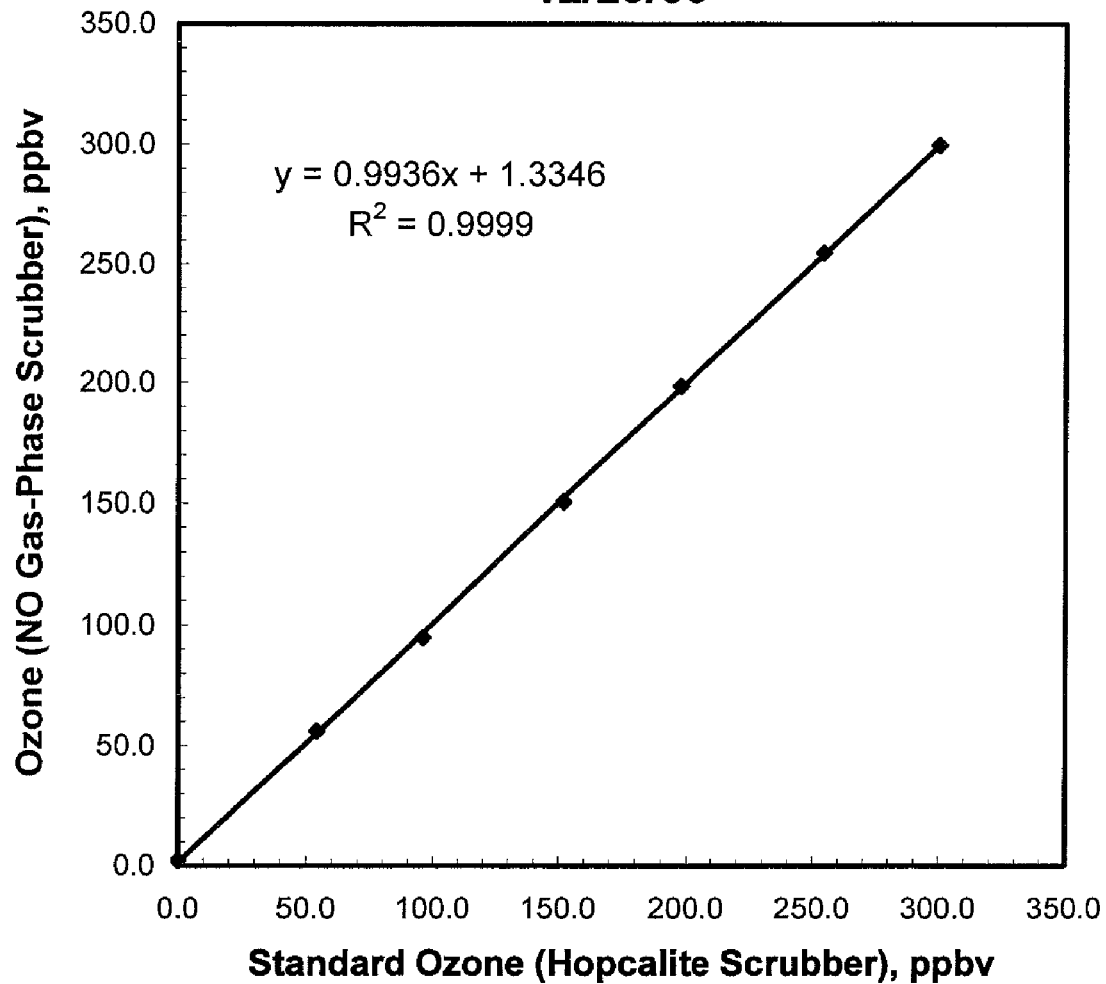
FIG. 5 is a calibration curve obtained using nitric oxide as a gas-phase scrubber.

An UV ozone monitor was modified according to FIG. 2 in which the hopcalite solid-phase scrubber was replaced by a gas-phase scrubber. The reagent gas was 195.7 ppm nitric oxide dilute in nitrogen. The reagent gas flow rate was 20 cc/min, and the total flow rate was 615 cc/min. The reaction volume was 30 cm$^3$, producing a reaction time of 2.9 s. Ozone was produced in a calibration manifold by use of a low pressure mercury lamp at mixing ratios of 0, 56, 98, 154, 200, 256 and 302 ppb. The ozone mixing ratios were simultaneously measured by the 2B Technologies Model 205, Serial No. 322DB Reference Ozone Monitor and the modified ozone monitor having a gas-phase scrubber. Ten measurements were made at each ozone mixing ratio. The Reference Ozone Monitor had been previously calibrated against a NIST-calibrated Thermo Electron Corp. Model 49i-PS Ozone Calibrator Primary Standard. Ozone concentrations in the ozone monitor having a gas-phase scrubber were calculated from first principles using the Beer-Lambert Law of equation 1 and multiplied by a factor of 1.017 to correct for dilution of the sample gas by the NO reagent gas. FIG. 5 is a plot of the measured ozone mixing ratios for the ozone monitor with gas-phase scrubber versus the ozone mixing ratios measured using the Reference Ozone Monitor. The slope of the linear regression line is 0.9936, the y intercept is 1.3 ppb, and the correlation coefficient, $R^2$, is 0.9999. This slope and intercept is well within the accuracy and precision of the Reference Ozone Monitor. The average precision of the, data for the modified ozone monitor with gas-phase scrubber was 0.82 ppb as compared to 1.33 ppb for the Reference Ozone Monitor. This experiment clearly demonstrates the measurement of ozone with high accuracy and precision using an ozone monitor utilizing NO as a gas phase scrubber.

While a number of exemplary aspects and embodiments have been discussed above, those of skill in the art will recognize certain modifications, permutations, additions and sub-combinations therefore. It is therefore intended that the following appended claims hereinafter introduced are interpreted to include all such modifications, permutations, additions and sub-combinations are within their true spirit and scope. Each apparatus embodiment described herein has numerous equivalents.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Whenever a range is given in the specification, all intermediate ranges and subranges, as well as all individual values included in the ranges given are intended to be included in the disclosure. When a Markush group or other grouping is used herein, all individual members of the group and all combinations and subcombinations possible of the group are intended to be individually included in the disclosure.

In general the terms and phrases used herein have their art-recognized meaning, which can be found by reference to standard texts, journal references and contexts known to those skilled in the art. The above definitions are provided to clarify their specific use in the context of the invention.

All patents and publications mentioned in the specification are indicative of the levels of skill of those skilled in the art to which the invention pertains. All references cited herein are hereby incorporated by reference to the extent that there is no inconsistency with the disclosure of this specification. Some references provided herein are incorporated by reference herein to provide details concerning additional starting materials, additional methods of synthesis, additional methods of analysis and additional uses of the invention.

CITED LITERATURE

Bognar, J. A. and Birks, J. W. (1996) "Miniaturized Ultraviolet Ozonesonde for Atmospheric Measurements," *Analytical Chemistry* 68, 3059-3062.

Hudgens, E. E., Kleindienst, T. E., McElroy, F. F., Ollison, W. M. (1994) "A study of interferences in ozone UV and chemiluminescent monitors. In *International Symposium on Measurement of Toxics and Related Air Pollutants*, Research Triangle park, N.C.; Proceedings of the Air and Waste Management Association; VIP-39, Air and Waste Management Association: Pittsburgh, Pa., pp 405-415.

Kleindienst, T. E., Hudgens, E. E., Smith, D. F., McElroy, F. F. and Bufalini, J. J. (1993) "Comparison of chemiluminescence and ultraviolet ozone monitor responses in the presence of humidity and photochemical pollutants, *Air and Waste Management Association* 43, 213-222.

Kleindienst, T. E., McIver, C. D., Ollison, W. M. (1997) "A study of interferences in ambient ozone monitors." In *International Symposium on Measurement of Toxics and Related Air Pollutants*, Research Triangle Park, N.C.; *Proceedings of Air and Waste Management Association*; VIP-74, Air and Waste Management Association: Pittsburgh, Pa., pp 215-225.

Leston, A. and Ollison, W. (1993) "Estimated accuracy of ozone design values: are they compromised by method interference?," In Tropospheric Ozone: *Nonattainment and Design Value Issues*, Boston, Mass.; *Proceedings of Air and Waste Management Association*; TR-23, Air and Waste Management Association: Pittsburgh, Pa., 1993; pp 451-456.

Leston, A. R., Ollison, W. M.; Spicer, C. W.; Satola, J. (2005) "Potential interference bias in ozone standard compliance monitoring." In *Symposium on Air Quality Measurement Methods and Technology, Proceedings of the AMMA Specialty Conference*, VIP126-CD, Research Triangle Park, N.C., Air and Waste Management Association: Pittsburgh, Pa., 2005.

Li, Y., Lee, S-R. and Wu, C-Y. (2006) "UV-absorption-based measurements of ozone and mercury: An investigation on their mutual interferences," *Aerosol and Air Quality Research* 6, 418-429.

Maddy, J. A. (1998) "A test that identifies ozone monitors prone to anomalous behavior while sampling hot and humid air. In Air and Waste Management Association Annual Meeting, San Diego, Calif.; *Proceedings of Air and Waste Management Association*; Air and Waste Management Association: Pittsburgh, Pa.

Maddy, J. A. (1999) "Evaluating a heated metal scrubber's effectiveness in preventing ozone monitor's anomalous behavior during hot and humid ambient sampling." In Air and Waste Management Association Annual Meeting, St. Louis, Mo.; *Proceedings of Air and Waste Management Association*; Air and Waste Management Association: Pittsburgh, Pa., 1999.

Meyer, C. P., Elsworth, C. M. and Galbally, I. E. (1991) "Water vapor interference in the measurement of ozone in ambient air by ultraviolet absorption," *Review of Scientific Instruments* 62, 223-228.

NASA (2006) Chemical Kinetics and Photochemical Data for Use in Atmospheric Studies, Evaluation Number 15, NASA Panel on Data Evaluation, Jul. 10, 2006.

U.S. Environmental Protection Agency (1999) *Laboratory Study to Explore Potential Interferences to Air Quality Monitors*, EPA-454/C-00-002. Office of Air Quality Planning and Standards: Research Triangle Park, N.C.

Wilson, K. L. and Birks, J. W. "Mechanism and Elimination of a Water Vapor Interference in the Measurement of Ozone by UV Absorbance," *Environmental Science and Technology* 40, 6361-6367 (2006)."

We claim:

1. A method of improving the measurement of the concentration of ozone in a continuously flowing sample of gas, the method comprising the steps of:
   providing a detection chamber having a light source on one side and a light sensing detector on the opposing side functioning to detect the amount of ozone in the gas sample;
   providing a gas phase ozone scrubber in the flow path of the gas sample before the ozone detection chamber;
   the gas phase ozone scrubber supplying a gas phase substance which reacts with ozone, said gas phase substance reacting with the ozone to substantially reduce the concentration of ozone in a selected portion of the sample;
   providing a means to produce a sample of gas in which the ozone has been substantially reduced in the ozone scrubber and an unaltered sample of gas;
   measuring the light intensity at the detector when the sample gas in which the ozone has been destroyed in the detection chamber;
   measuring the light intensity at the detector when the unaltered sample of gas is in the detection chamber; and
   using a Beer-Lambert law to calculate the ozone concentration within the detection cell.

2. The method of claim 1, wherein the gas phase substance is NO.

3. The method of claim 2, wherein NO is produced by photolysis.

4. The method of claim 1, wherein the gas phase substance is Br.

5. The method of claim 4 wherein the Br is produced by photolysis.

6. The method of claim 1 wherein the percentage of ozone scrubbed is more than 90%.

7. The method of claim 6 wherein the percentage of ozone scrubbed is more than 98%.

8. The method of claim 1 further comprising the step of determining the pressure and temperature within the detection chamber and using the pressure and temperature with the concentration of ozone to express the ozone mixing ratio in terms of parts-per-billion by volume.

9. A photometer apparatus for detecting a concentration of ozone in a gas sample, the photometer comprising:
   a means to draw a gas sample into the photometer;
   a detection chamber having a light source on one side and a light sensing detector on the opposing side functioning to detect the amount of ozone in the gas sample;
   a gas phase ozone scrubber;
   a first and second flow path in parallel connecting to the detection chamber;
   the second flow path having the gas phase ozone scrubber to substantially reduce the ozone from a portion of the gas sample to form a reference gas sample;
   a flow directing means functioning to direct the gas sample through the first or second flow path to the detection chamber;
   the flow direction means functioning to direct the gas sample through the other flow path after a chosen amount of time;

a means to compare a value calculated by the light sensing detector when the gas sample flowed through the first flow path with a value to calculated by the light sensing detector when the gas sample flowed through the second flow path to calculate the concentration of ozone; and wherein a mixing ratio of ozone is calculated using Beer-Lambert law.

10. The apparatus of claim 9, wherein the gas phase ozone scrubber uses NO.

11. The apparatus of claim 9, wherein the gas phase ozone scrubber uses Br.

12. The apparatus of claim 9, wherein a reagent gas within the gas phase ozone scrubber is created via photolysis.

13. The apparatus of claim 9 further comprising a pressure sensor and a temperature sensor in contact with the detection chamber.

14. The apparatus of claim 9 further comprising a flow path for the gas sample connecting to the detection chamber;

the flow path having a connection to the gas phase ozone scrubber;

a control to allow the gas phase substance into the flow path for a selected amount of time to substantially reduce the ozone from a portion of the gas sample to form a reference gas sample;

a means to compare a value calculated by the light sensing detector by an unaltered gas sample with a value to calculated by the light sensing detector by the reference gas sample to calculate the concentration of ozone.

15. The apparatus of claim 14 wherein a mixing ratio of ozone is calculated using Beer-Lambert law.

16. The apparatus of claim 14, wherein the gas phase ozone scrubber uses NO.

17. The apparatus of claim 14, wherein the gas phase ozone scrubber uses Br.

18. The apparatus of claim 15 further comprising a pressure sensor and a temperature sensor in contact with the detection chamber.

* * * * *